United States Patent
Price et al.

(10) Patent No.: US 10,918,043 B2
(45) Date of Patent: Feb. 16, 2021

(54) *GYPSOPHILA* PLANTS HAVING ELEVATED AMOUNT OF BETA-CAROTENE AND METHODS FOR OBTAINING THE SAME

(71) Applicant: DANZIGER "DAN" FLOWER FARM, Mishmar HaShiva (IL)

(72) Inventors: Hadas Price, Givat Yeshayahu (IL); Amir Zuker, Nes Ziona (IL); Gavriel Danziger, Nir Zvi (IL)

(73) Assignee: DANZIGER "DAN" FLOWER FARM, Mishmar Hashiva (IL)

( * ) Notice: Subject to any disclaimer, the term of this patent is extended or adjusted under 35 U.S.C. 154(b) by 439 days.

(21) Appl. No.: 15/537,536

(22) PCT Filed: Dec. 23, 2015

(86) PCT No.: PCT/IL2015/051250
§ 371 (c)(1),
(2) Date: Jun. 19, 2017

(87) PCT Pub. No.: WO2016/103266
PCT Pub. Date: Jun. 30, 2016

(65) Prior Publication Data
US 2017/0367281 A1 Dec. 28, 2017

Related U.S. Application Data

(60) Provisional application No. 62/096,098, filed on Dec. 23, 2014.

(51) Int. Cl.
| | |
|---|---|
| *A01H 6/30* | (2018.01) |
| *A01H 5/02* | (2018.01) |
| *A01H 3/04* | (2006.01) |
| *A01G 7/06* | (2006.01) |
| *A01H 1/04* | (2006.01) |
| *A01H 5/10* | (2018.01) |
| *C12N 9/00* | (2006.01) |

(52) U.S. Cl.
CPC .............. *A01H 6/30* (2018.05); *A01G 7/06* (2013.01); *A01H 1/04* (2013.01); *A01H 3/04* (2013.01); *A01H 5/02* (2013.01); *A01H 5/10* (2013.01); *C12N 9/00* (2013.01)

(58) Field of Classification Search
CPC ........................................................ A01H 6/30
USPC .......................................................... Plt./354
See application file for complete search history.

(56) References Cited

U.S. PATENT DOCUMENTS

| | | | |
|---|---|---|---|
| PP10,964 P * | 6/1999 | Danziger ....................... | Plt./354 |
| 7,750,209 B2 * | 7/2010 | Tanaka ................. | C12N 15/825 |
| | | | 435/320.1 |

FOREIGN PATENT DOCUMENTS

| | | |
|---|---|---|
| CN | 101171913 A | 5/2008 |
| EP | 0993776 A1 | 4/2000 |
| WO | 2014070646 A1 | 5/2014 |
| WO | WO 2014/070646 A1 * | 5/2014 |

OTHER PUBLICATIONS

Waterland, Nicole L., "Benzyladenine and gibberellic acid application prevents abscisic acid-induced leaf chlorosis in pansy and viola"; HortScience, vol. 45 No. 6, pp. 925-933; Jun. 30, 2010.
Ben Zvi MM., "Agrobacterium-mediated transformation of *Gypsophila* (*Gypsophila paniculata* L.)"; Molecular Breeding, vol. 22, No. 4, pp. 543-553; Jun. 20, 2008.
Kanayama Y., "Genetic and Molecular Aspects of Gypsophila"; Genes, Genomes and Genomics, vol. 1, No. 1, pp. 63-65; Dec. 31, 2007.
Kishi F., "Production of an interspecific hybrid in Gypsophila by ovule-embryo culture"; Euphytica, vol. 74, pp. 85-90; 1994.
Darwent AL. and Coupland RT., "Life history of Gypsophila paniculata"; Weeds vol. 14, pp. 313-318; 1966.
Ichimura K., "Extension of the vase life in cut roses by treatment with glucose, isothiazolinonic germicide, citric acid and aluminum sulphate solution"; JARQ. vol. 40, No. 3, pp. 263-269; 2006.
International Search Report, dated Jun. 30, 2016.
Written Opinion of the International Search Authority, dated Jun. 30, 2016.
Cheong, Dong Chun et al: "Effects of harvesting time on flowering and cut-flower quality of Gypsophila paniculata", Journal of the Korean society for horticultural science, vol. 43, No. 3, pp. 376-380, Jun. 1, 1999.
Martinez-Mateo, Cesar A. et al.: "Carnation Vase Life as Affected by Gibberellic Acid and Benzyladenine Treatments.", Hortscience, vol. 39, No. 4, Jul. 31, 2004 (Jul. 31, 2004), pp. 824-824.
Zvi, Michal Moyal Ben et al: "PAP1 transcription factor enhances production of phenylpropanoid and terpenoid scent compounds in rose flowers.", New Phytologist, vol. 195, No. 2, Apr. 30, 2012 (Apr. 30, 2012), pp. 335-345.

(Continued)

*Primary Examiner* — David H Kruse

(74) *Attorney, Agent, or Firm* — The Roy Gross Law Firm, LLC; Roy Gross

(57) ABSTRACT

The present invention provides an altered *Gypsophila* plant comprising a flower having an altered phenotype, wherein the flower having an altered phenotype comprises an elevated amount of Beta-Carotene, wherein the elevated amount of Beta-Carotene is at least twice the concentration of Beta-Carotene compared to the concentration of Beta-Carotene in a control *Gypsophila* flower and to methods for selecting altered *Gypsophila* plants.

7 Claims, 1 Drawing Sheet

(56) References Cited

OTHER PUBLICATIONS

Clotault, Jeremy.: "Les Carotenoides", Espace Pedagogique Claroline, Aug. 4, 2011 (Aug. 4, 2011), Retrieved from the Internet <mon.univmontp2.fr/claroline/backends/download.phpurl=L2Nhcm90ZW5vaWRIc_18wNSYwOC0wNC0yMDExLnBkZg%3D%3D&cidReset=true&cidReq=FLBI456_001> [retrieved on Apr. 8, 2011].

Emumi H. et al: "Study on Lily Longevity Treated with Growth Regulator (GA and BA) by Path Analysis"; American Eurasian J Agric Environ Sci, 2011, vol. 10, No. 5, pp. 814-820.

\* cited by examiner

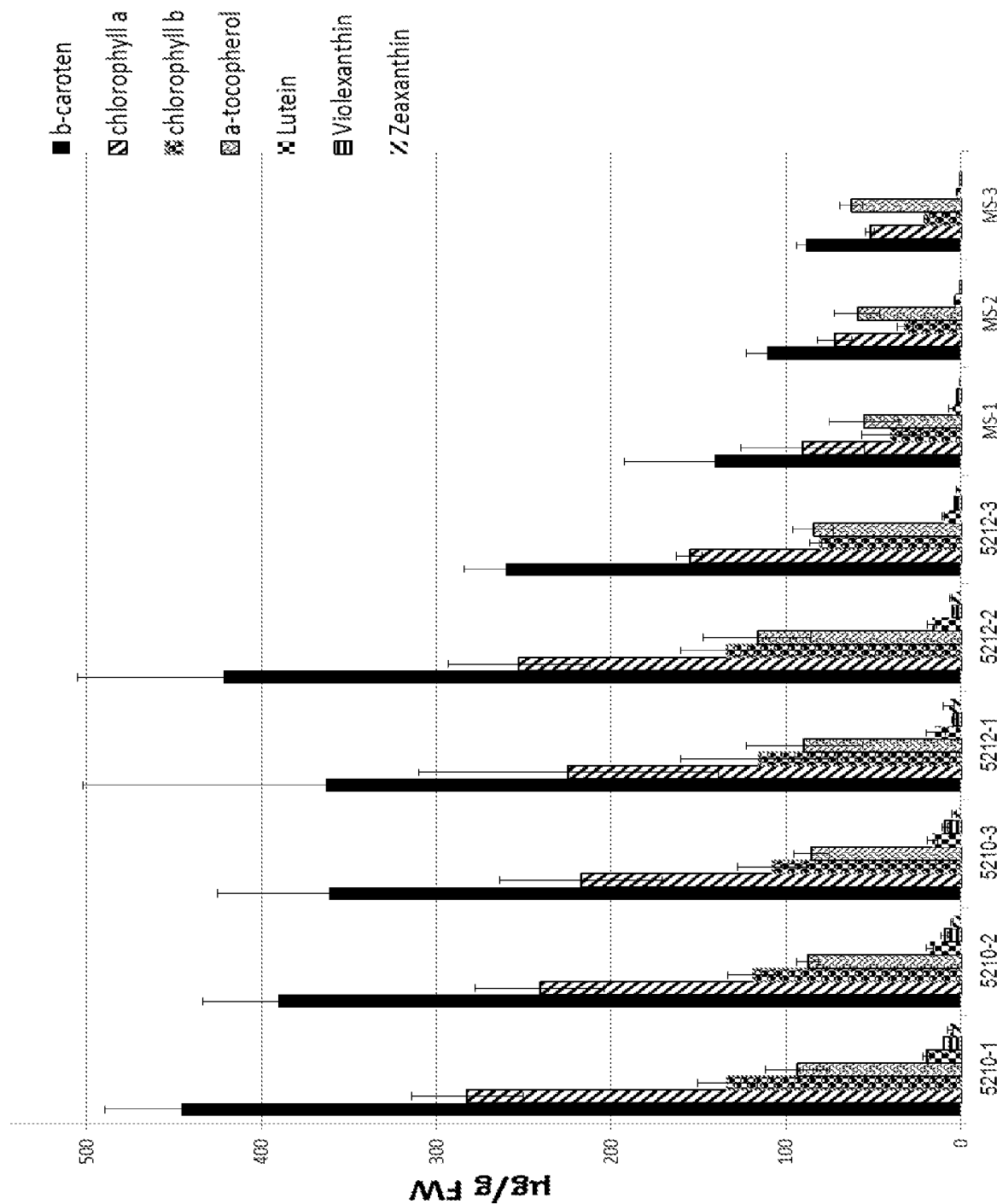

GYPSOPHILA PLANTS HAVING ELEVATED AMOUNT OF BETA-CAROTENE AND METHODS FOR OBTAINING THE SAME

CROSS-REFERENCE TO RELATED APPLICATIONS

This application is a National Stage Application of PCT Patent Application No. PCT/IL2015/051250, filed Dec. 23, 2015, which claims the benefit of priority of U.S. Provisional Patent Application No. 62/096,098, filed Dec. 23, 2014, entitled GYPSOPHILA PLANTS HAVING ELEVATED AMOUNT OF BETA-CAROTENE AND METHODS FOR OBTAINING THE SAME. The contents of the above applications are all incorporated by reference as if fully set for herein in their entirety.

FIELD OF INVENTION

This invention is directed to; inter alia, to an altered Gypsophila plant accumulating elevated amount of a carotenoid and/or pigment and methods and composition for obtaining the same.

BACKGROUND OF THE INVENTION

G. paniculata originated in Europe, temperate Asia and the eastern Mediterranean. It was first introduced into North America before 1890 as a garden ornamental and is often cultivated in gardens, flower beds and in prepared bouquets (Cavers, 1995; Darwent and Coupland, 1966).

The genus Gypsophila, flowering plants, is a member of the Cariophyllaceae family. It is a large family consists of 88 genera and some 2,000 species. Gypsophlia consists of 125 known species (Shillo, 1985), which are annuals, biennials and perennials. G. paniculata, first described in Linne's "species Plantarum", is an herbaceous perennial plant that is sometimes used as an annual crop. The chromosome number of the G. paniculata is 2n=34 (Kishi, 1994). The genus name is from the Greek gypsos ("gypsum") and philios ("loving").

In the horticultural industry, Gypsophila plants are found in a variety of forms for landscape, home gardens, container use and cut flowers. G. paniculaca is the major Gypsophila species used for cut flowers (Darwent and coupland, 1966; Shillo, 1985; Moyal-Ben Zvi, et. al., 2008), it is traditionally used as a filler flower to lend fullness and visual interest to ornamental bouquets and floral arrangements. To date, conventionally bred Gypsophila is available in predominately one color, white, and in very limited varieties, light pink.

Moreover, the Gypsophila plants are annual and perennial plants. The Gypsophila stems are usually erect and branching or sprawling, or in a few species prostrate along the ground. The leaves are variable in shape. The inflorescence is usually a cyme or a thyrse, branching intricately. Each small flower has a cup-like calyx of white-edged green sepals containing five petals in shades of white or pink. The fruit is a rounded or oval capsule opening at valves. It contains several brown or black seeds which are often shaped like a kidney or a snail shell.

SUMMARY OF THE INVENTION

In one embodiment, the present invention provides an altered Gypsophila plant comprising a flower having an altered phenotype, wherein the flower having an altered phenotype comprises an elevated amount of Beta-Carotene, wherein the elevated amount of Beta-Carotene is at least 2 times the concentration of Beta-Carotene compared to the concentration of Beta-Carotene in a control Gypsophila flower. In some embodiments, a control Gypsophila is Gypsophila cv. Million Stars. In some embodiments, Gypsophila flower is at anthesis. In some embodiments, Gypsophila flower is at the closed bud phase.

In another embodiment, the present invention further provides a method for screening a population of parent Gypsophila plants for the presence therein of individual plants capable of producing offspring plants having a flower with an altered phenotype, wherein the flower having an altered phenotype comprises an elevated amount of Beta-Carotene, wherein the elevated amount of Beta-Carotene is at least 2 times the concentration of Beta-Carotene compared to the concentration of Beta-Carotene in a control Gypsophila, comprising: (a) preparing cut flowers from the individual parent plants; and (b) contacting each cut flower from a parent Gypsophila plant with a composition comprising water, 10 to 50 mg/l Gibberellic acid, and 5 to 20 mg/l benzyl adenine, for at least 2 days, wherein a flower developing petals having yellow, cream or both color as oppose to white is selected as having an altered phenotype. In some embodiments, at least 15% of a petal's surface area of a flower having an altered phenotype is green. In some embodiments, 10% or 15% of a petal's surface area of a flower having an altered phenotype is yellow. In some embodiments, 5%, 10%, 15%, or 20% of a petal's surface area of a flower having an altered phenotype is white.

In another embodiment, yellow is light yellow. In another embodiment, yellow is a color having a wavelength of between 570 to 580 nm. In another embodiment, yellow is a pale tint of yellow. In another embodiment, yellow is lemon chiffon. In another embodiment, yellow is pigment yellow. In another embodiment, yellow is canary yellow. In another embodiment, yellow is mellow yellow. In another embodiment, yellow is any yellow known to one of skill in the art.

In another embodiment, the present invention further provides a plant or an offspring of a plant. comprising a flower having an altered phenotype, wherein the flower having an altered phenotype comprises an elevated amount of Beta-Carotene, wherein the elevated amount of Beta-Carotene is at least twice the concentration of Beta-Carotene compared to the concentration of beta-Carotene in a control Gypsophila flower In another embodiment, the present invention further provides a composition comprising: water, 10 to 50 mg/l Gibberellic acid, and 5 to 20 mg/l benzyl adenine. In another embodiment, this composition is used for selection according to the invention. In another embodiment, this composition is for selecting a plant having elevated amount of Beta-Carotene.

BRIEF DESCRIPTION OF THE DRAWINGS

FIG. 1: Is a bar graph showing the amount of a pigment, carotenoids or both in micrograms per gram flower.

DETAILED DESCRIPTION OF THE INVENTION

In one embodiment, the present invention provides a unique Gypsophila plant having extended shelf life. In one embodiment, the present invention provides a unique Gypsophila plant having extended vase life. In one embodiment, the present invention provides a cultivated Gypsophila having favorable and unique characteristics such as shelf life. In another embodiment, the present invention provides a cultivated *Gypsophila* which is a product of an unexpected selection procedure.

In another embodiment, the present invention provides that the unique *Gypsophila* plant accumulates large and unexpected amounts of a plant pigment in comparison to a parallel wild type or other known *Gypsophila* plant. In another embodiment, the present invention provides that the unique *Gypsophila* plant accumulates at least twice the amount of a plant pigment in comparison to a parallel wild type or other known *Gypsophila* plant. In another embodiment, the term "altered" and "unique" are used interchangeably. In another embodiment, an altered plant has an altered or a unique phenotype in comparison to a parallel wild type or other known *Gypsophila* plant of the same species. In another embodiment, an altered plant has an altered petal characterized by a unique color or a combination of colors. In another embodiment, a "plant" or "a plant part" as used herein includes: seeds, leaves, stems, pollens, roots, root tips, anthers, ovules, petals, flowers, unrooted cutting, cutting and embryos. In another embodiment, a "plant" is a cutting. In another embodiment, a "plant" is a plant harvested for sale. In another embodiment, a "plant" or a "plant part" is an unrooted cutting.

In another embodiment, a "plant" is the entire plant including all the plant's organs. In another embodiment, a "plant" refers to plant cells or plant parts from which *Gypsophila paniculata* plants can be generated, including tissue culture, plant protoplasts, plant calli, plant clumps, and plant cells that are intact in plants. In another embodiment, a "plant" or "*Gypsophila*" is *Gypsophila paniculata*.

In another embodiment, the phrases "altered plant" and "plant of the invention" are used interchangeably. In another embodiment, "*Gypsophila*" and/or "altered plant" and/or the "plant of the invention" is a *Gypsophila*. In another embodiment, "*Gypsophila*" and/or "altered plant" and/or the "plant of the invention" is a *Gypsophila* characterized by elevated amounts of a plant pigment. In another embodiment, "*Gypsophila*" and/or "altered plant" and/or the "plant of the invention" is a *Gypsophila* characterized by elevated amounts of a combination of plant pigments. In another embodiment, "*Gypsophila*" and/or "altered plant" and/or the "plant of the invention" is a *Gypsophila* characterized by unexpected flower phenotype such as but not limited to green petals, yellow petals, and/or orange petals. In another embodiment, "*Gypsophila*" and/or "altered plant" and/or the "plant of the invention" is a *Gypsophila* characterized by unexpected and prolonged shelf life. In another embodiment, "*Gypsophila*" and/or "altered plant" and/or the "plant of the invention" is a *Gypsophila* is a flower. In another embodiment, "*Gypsophila*" and/or "altered plant" and/or the "plant of the invention" is a *Gypsophila* during anthesis or at the closed bud phase. In another embodiment, "*Gypsophila*" and/or "altered plant" and/or the "plant of the invention" is a *Gypsophila* during anthesis or at the closed bud phase. In another embodiment, "*Gypsophila*" and/or "altered plant" and/or the "plant of the invention" is a *Gypsophila* developing petals comprising cream color and/or yellow color when the cut flowers derived from the "*Gypsophila*" and/or "altered plant" and/or the "plant of the invention" are contacted with a screening composition as described herein.

In another embodiment, the phrases: "a plant of the invention", "an altered plant" and "a plant having a flower with an altered phenotype" are used interchangeably. In another embodiment, "an altered plant" or "a plant having a flower with an altered phenotype" has an altered or a unique phenotype in comparison to a parallel wild type or other known *Gypsophila* plant (control). In another embodiment, "an altered plant" or "a plant having a flower with an altered phenotype" has an altered or a unique phenotype in comparison to a parallel *Gypsophila* plant of the same species (control). In another embodiment, a plant of the invention and a control plant are *Gypsophila* plants. In another embodiment, a plant of the invention and a control plant are *Gypsophila* plants of the same species or of different species. In another embodiment, a plant of the invention and a control plant are compared, according to the invention, at the same developmental stage. In another embodiment, a plant of the invention and a control plant are compared, according to the invention, at the same developmental stage. In another embodiment, a plant of the invention and a control plant are assayed with respect to carotenoids contents, pigments contents, chlorophylls contents, or any combination thereof, at the same developmental stage. In another embodiment, a developmental stage is any flower developmental stage known to one of skill in the art. In another embodiment, a developmental stage is anthesis or closed bud phase.

In another embodiment, the amount of a chlorophyll and/or a carotenoid and/or a pigment is quantified in a petal. In another embodiment, the amount of a chlorophyll and/or a carotenoid and/or a pigment is quantified in a flower. In another embodiment, the amount of chlorophylls, carotenoids and/or pigments is quantified from a white flower. In another embodiment, the amount of chlorophylls, carotenoids and/or pigments is quantified from a white petal. In another embodiment, the amount of chlorophylls, carotenoids and/or pigments is quantified from multiple flowers derived from a single plant. In another embodiment, the amount of chlorophylls, carotenoids and/or pigments is quantified from multiple flowers derived from multiple plants. In another embodiment, the amount of chlorophylls, carotenoids and/or pigments is quantified from multiple flowers derived from multiple plants having the same phenotype as described herein.

In another embodiment, "flower" is any flower or flower type known to one of in the art. In another embodiment, "flower" is a multi-flower. In another embodiment, "flower" is a single flower. In another embodiment, "flower" is a double-flower. In another embodiment, "flower" is a semi-double flower.

In another embodiment, the plant of the invention comprises at least 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.4, 3.6, 3.8, 4.0, 4.2, 4.4, 4.6, 4.8, 5.0, 5.5, 6.0, 6.5, 7.0, 7.5, 8.0, 8.5, 9.0, 9.5, or 10.0 times the concentration and/or amount of a certain pigment and/or chlorophylls, carotenoid and/or combination of pigments and/or combination of pigments and chlorophylls, compared to a control plant. In another embodiment, the plant of the invention comprises at least twice the concentration and/or amount of a certain pigment and/or chlorophylls and/or carotenoid and/or combination of pigments and/or combination of pigments and carotenoids compared to a control plant. In another embodiment, the plant of the invention comprises 1.5 times to 15 times the concentration and/or amount of a certain pigment and/or chlorophylls and/or carotenoid and/or combination of pigments and/or combination of pigments chlorophylls and/or carotenoids compared to a control plant. In another embodiment, the plant of the invention comprises 1.5 times to 5 times the concentration and/or amount of a certain pigment and/or chlorophylls and/or carotenoid and/or combination of pigments and/or combination of pigments and chlorophylls and/or carotenoids compared to a control plant. In another embodiment, the plant of the invention comprises 2 times to 10 times the concentration and/or amount of a certain pigment and/or chlorophylls and/or carotenoid and/or combination of pigments and/or combination of pigments and chlorophylls and/or carotenoids compared to a control plant. In another embodiment, the plant of the invention comprises 2 times to 5 times the concentration and/or amount of a certain pigment and/or chlorophylls and/or carotenoid and/or combination of pigments and/or combination of pigments and chlorophylls and/or carotenoids compared to a control plant. In another embodiment, the plant of the invention comprises 3 times to 8 times the concentration and/or amount of a certain pigment and/or chlorophylls and/or carotenoid and/or combination of pigments and/or combination of pigments and chlorophylls and/or carotenoids compared to a control plant such as but not limited to *Gypsophila* million stars.

In another embodiment, a control plant is a wild-type plant of the same species. In another embodiment, a control plant is any *Gypsophila* plant known prior to the date of the present invention. In another embodiment, a control plant is *Gypsophila* million stars. In another embodiment, a control plant is any cultivated or selected plant of the same species. In another embodiment, a control plant is any known *Gypsophila*. In another embodiment, a control plant is any known *Gypsophila* at anthesis or at the closed bud phase. In another embodiment, a control plant is any known *Gypsophila* flower. In another embodiment, a control plant is any known *Gypsophila* flower at anthesis or at the closed bud phase. In another embodiment, 'the plant of the invention" is a *Gypsophila* flower. In another embodiment, the plant of the invention a *Gypsophila* flower at anthesis or at the closed bud phase. In another embodiment, 'the plant of the invention" is a flower having an altered phenotype. In another embodiment, 'the plant of the invention" is a plant having an altered phenotype. In another embodiment, 'altered phenotype" is *Gypsophila* altered phenotype. In another embodiment, 'altered phenotype" is *Gypsophila* flower altered phenotype.

In another embodiment, the pigment is a photosynthetic pigment. In another embodiment, the pigment is chlorophyll A. In another embodiment, the pigment is chlorophyll B. In another embodiment, the pigment is a carotenoid. In another embodiment, the pigment is a xanthophyll. In another embodiment, the pigment is Lutein. In another embodiment, the pigment is Beta-Carotene. In another embodiment, the pigment is Antheraxanthin. In another embodiment, the pigment is zeaxanthin. In another embodiment, the pigment is Violaxanthin. In another embodiment, an altered *Gypsophila* plant of the invention comprises 1.2 times to 18 times the concentration and/or amount of: chlorophyll A, chlorophyll B, xanthophyll, a carotenoid, a pigment, Lutein, Beta-Carotene, Antheraxanthin, zeaxanthin, Violaxanthin, or any combination thereof. In another embodiment, an altered *Gypsophila* plant of the invention comprises 1.2 times to 15 times the concentration and/or amount of: chlorophyll A, chlorophyll B, xanthophyll, a carotenoid, a pigment, Lutein, Beta-Carotene, Antheraxanthin, zeaxanthin, Violaxanthin, or any combination thereof. In another embodiment, an altered *Gypsophila* plant of the invention comprises 1.2 times to 10 times the concentration and/or amount of: chlorophyll A, chlorophyll B, xanthophyll, a carotenoid, a pigment, Lutein, Beta-Carotene, Antheraxanthin, zeaxanthin, Violaxanthin, or any combination thereof.

In another embodiment, the phrase "an altered *Gypsophila* plant of the invention" is synonymous with "altered petals" or "altered carotenoids and/or pigment content" or "altered flower" or "a flower having altered carotenoids and/or pigment content" or a "*Gypsophila* plant comprising a flower having an altered phenotype".

In another embodiment, the altered *Gypsophila* plant of the invention, comprises an elevated amount of Beta-Carotene, wherein elevated amount of Beta-Carotene is at least 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.4, 3.6, 3.8, 4.0, 4.2, 4.4, 4.6, 4.8, 5.0, 5.5, 6.0, 6.5, 7.0, 7.5, 8.0, 8.5, 9.0, 9.5, or 10.0 times the concentration of Beta-Carotene in a control *Gypsophila* flower. In another embodiment, the altered *Gypsophila* plant of the invention, comprises an elevated amount of chlorophyll A, wherein elevated amount of chlorophyll A is at least twice the concentration of chlorophyll A in *Gypsophila* cv. Million Stars (M.S) flower at anthesis or at the closed bud phase. In another embodiment, the flower having an altered phenotype further comprises an elevated amount of chlorophyll B, wherein elevated amount of chlorophyll B is at least 2 times the concentration of chlorophyll B in *Gypsophila* cv. Million Stars (M.S) flower at anthesis or at the closed bud phase. In another embodiment, the flower having an altered phenotype comprises from 0.5 to 4% w/w or v/v Lutein of the total carotenoid content in a petal. In another embodiment, the flower having an altered phenotype comprises from 30 to 50% w/w or v/v Beta-Carotene of the total carotenoid content in a petal. In another embodiment, the flower having an altered phenotype further comprises an elevated amount of Zeaxanthin, wherein elevated amount of Zeaxanthin is at least 10 times the concentration of Zeaxanthin in *Gypsophila* cv. Million Stars (M.S) flower at anthesis or at the closed bud phase. In another embodiment, the flower having an altered phenotype comprises an elevated amount of Violaxanthin, wherein elevated amount of Violaxanthin is at least 1.5 times the concentration of Violaxanthin in *Gypsophila* cv. Million Stars (M.S) flower at anthesis or at the closed bud phase.

In another embodiment, at least 10%, 11%, 12%, 13%, 14%, 15%, 16%, 18%, 20%, 25%, 30%, 35%, 40%, 45%, 50%, 55%, or 60% of a petal's surface area of the flower having an altered phenotype is green, yellow, orange or any combination thereof. In some embodiments, at least 15% of a petal's surface area of a flower having an altered phenotype is green. In some embodiments, at least 17% of a petal's surface area of a flower having an altered phenotype is green. In some embodiments, at least 20% of a petal's surface area of a flower having an altered phenotype is green. In some embodiments, at least 22% of a petal's surface area of a flower having an altered phenotype is green. In some embodiments, at least 25% of a petal's surface area of a flower having an altered phenotype is green. In some embodiments, at least 30% of a petal's surface area of a flower having an altered phenotype is green. In some embodiments, at least 40% of a petal's surface area of a flower having an altered phenotype is green. In some embodiments, at least 40% of a petal's surface area of a flower having an altered phenotype is green. In another embodiment, at least 5%, 8%, 10%, 15%, 20%, 25%, 30%, 35%, 40%, 45%, 0r 50% of a petal surface area of the flower having an altered phenotype is white, yellow, or both. In another embodiment, control *Gypsophila* flower is *Gypsophila* cv. Million Stars flower. In another embodiment, a flower as described herein is at anthesis or is at the closed bud phase.

In another embodiment, at least 1.4 times is at least 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9. 4.0, 4.1, or 4.2. 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 5, 5.5, 6, 6.5, 7, 7.5, 8, 8.5, 9, 9.5, 10, 10.5, 11, 12, 13, 14, 15, 16, 17, 18, 19 or 20. In another embodiment, at least 1.5 times is at least 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9. 4.0, 4.1, or 4.2. 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 5, 5.5, 6, 6.5, 7, 7.5, 8, 8.5, 9, 9.5, 10, 10.5, 11, 12, 13, 14, 15, 16, 17, 18, 19 or 20. In another embodiment, at least 2 times is at least 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9. 4.0, 4.1, 4.2. 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 5, 5.5, 6, 6.5, 7, 7.5, 8, 8.5, 9, 9.5, 10, 10.5, 11, 12, 13, 14, 15, 16, 17, 18, 19 or 20. In another embodiment, at least 2.5 times is at least 2.6, 2.7, 2.8, 2.9, 3.0, 3.1, 3.2, 3.3, 3.4, 3.5, 3.6, 3.7, 3.8, 3.9. 4.0, 4.1, 4.2. 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 5, 5.5, 6, 6.5, 7, 7.5, 8, 8.5, 9, 9.5, 10, 10.5, 11, 12, 13, 14, 15, 16, 17, 18, 19 or 20. In another embodiment, at least 10 times is at least 10.1, 10.2, 10.3, 10.4, 10.5, 11, 11.1, 11.2, 11.3, 11.4, 11.5, 12.0, 12.5, 13, 13.5, 14.0, 14.5, 15, 16, 17, 18, 19, 20, 21, 22, 23, 24, or 25. In another embodiment, at least 5% is 5.1%, 5.2%, 5.3%, 5.4%, 5.5%, 6%, 7%, 8%, 9%, 9.5% or 10%. In another embodiment, at least 10% is 10.1%, 10.2%, 10.3%, 10.4%, 10.5%, 11%, 12%, 13%, 14%, 15%, 16%, 17%, 18%, 19%, 20%, 22%, 24%, 25%, 26%, 28%, 30%, 32%, 34%, 35, 37%, 40%, 45, 50%, 55%, or 60%. In another embodiment, any range of percentages (%) of the present invention refers to w/w, w/v, v/w or v/v %.

In another embodiment, an altered *Gypsophila* plant of the invention comprises an elevated amount of chlorophyll A, wherein the elevated amount of chlorophyll A is at least 1.5 times the concentration of chlorophyll A compared to the concentration of chlorophyll A in a known *Gypsophila* (wild type or other known plant such as Million Stars as described herein). In another embodiment, an altered *Gypsophila* plant of the invention comprises an elevated amount of chlorophyll A, wherein the elevated amount of chlorophyll A is at least twice the concentration of chlorophyll A compared to the concentration of chlorophyll A in a known *Gypsophila* (wild type or other known plant such as Million Stars as described herein). In another embodiment, an altered *Gypsophila* plant of the invention comprises a flower having an elevated amount of chlorophyll A, wherein the elevated amount of chlorophyll A is at least twice the concentration of chlorophyll A compared to the concentration of chlorophyll A in a known *Gypsophila* flower (wild type or other known plant).

In another embodiment, the plant of the invention (with altered phenotype) comprises 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.6, 3.8, 4.0, 4.2, 4.4, 4.6, 4.8, 5.0, 5.5, 6.0, 6.5, 7.0, 7.5, 8.0, 8.5, 9.0, 9.5, or 10.0 times the concentration and/or amount of chlorophyll A compared to a control plant. In another embodiment, the plant of the invention comprises 1.5 times to 15 times the concentration and/or amount of chlorophyll A compared to a control plant. In another embodiment, the plant of the invention comprises 2 times to 10 times the concentration and/or amount of chlorophyll A compared to a control plant. In another embodiment, the plant of the invention comprises 1.5 times to 8 times the concentration and/or amount of chlorophyll A compared to a control plant. In another embodiment, the plant of the invention comprises at least twice the concentration and/or amount of chlorophyll A compared to a control plant. In another embodiment, the plant of the invention comprises at least four times the concentration and/or amount of chlorophyll A compared to a control plant. In another embodiment, the plant of the invention comprises at least five times the concentration and/or amount of chlorophyll A compared to a control plant. In another embodiment, the upper limit of the concentration and/or amount of chlorophyll A in a plant of the invention compared to a control plant is 15 times. In another embodiment, the upper limit of the concentration and/or amount of chlorophyll A in a plant of the invention compared to a control plant is 12 times. In another embodiment, the upper limit of the concentration and/or amount of chlorophyll A in a plant of the invention compared to a control plant is 10 times.

In another embodiment, the plant of the invention comprises 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.8, 4.0, 4.2, 4.4, 4.6, 4.8, 5.0, 5.5, 6.0, 6.5, 7.0, 7.5, 8.0, 8.5, 9.0, 9.5, or 10.0 times the concentration and/or amount of chlorophyll B compared to a control plant. In another embodiment, the plant of the invention comprises 2.6 times the concentration and/or amount of chlorophyll B compared to a control plant. In another embodiment, the plant of the invention comprises 1.2 times to 12 times the concentration and/or amount of chlorophyll B compared to a control plant. In another embodiment, the plant of the invention comprises at least 2.5 times the concentration and/or amount of chlorophyll B compared to a control plant. In another embodiment, the plant of the invention comprises at least twice the concentration and/or amount of chlorophyll B compared to a control plant. In another embodiment, the plant of the invention comprises at least 2.0 times the concentration and/or amount of chlorophyll B compared to a control plant. In another embodiment, the upper limit of the concentration and/or amount of chlorophyll B in a plant of the invention compared to a control plant is 12 times. In another embodiment, the upper limit of the concentration and/or amount of chlorophyll B in a plant of the invention compared to a control plant is 10 times. In another embodiment, the upper limit of the concentration and/or amount of chlorophyll B in a plant of the invention compared to a control plant is 8 times.

In another embodiment, the plant of the invention comprises 2 times to 12 times the concentration and/or amount of Lutein compared to a control plant. In another embodiment, the plant of the invention comprises 1.5, 1.8, 2.0, 2.1, 2.2, 2.3, 2.4, 2.5, 2.6, 2.7, 2.8, 2.9, 3.0, 3.1, 3.2, 3.3, 3.4, 3.6, 3.8, 4.0, 4.2, 4.4, 4.6, 4.8, 5.0, 5.5, 6.0, 6.5, 7.0, 7.5, 8.0, 8.5, 9.0, 9.5, or 10.0 times the concentration and/or amount of Lutein compared to a control plant. In another embodiment, the plant of the invention comprises 3 times to 8 times the concentration and/or amount of Lutein compared to a control plant. In another embodiment, the plant of the invention comprises at 1.5 times the concentration and/or amount of Lutein compared to a control plant. In another embodiment, the plant of the invention comprises at least twice the concentration and/or amount of Lutein compared to a control plant. In another embodiment, the plant of the invention comprises at 2.5 times the concentration and/or amount of Lutein compared to a control plant. In another embodiment, the upper limit of the concentration and/or amount of Lutein in a plant of the invention compared to a control plant is 12 times. In another embodiment, the upper limit of the concentration and/or amount of Lutein in a plant of the invention compared to a control plant is 10 times. In another embodiment, the upper limit of the concentration and/or amount of Lutein in a plant of the invention compared to a control plant is 8 times. In another embodiment, the upper limit of the concentration and/or amount of Lutein in a plant of the invention compared to a control plant is 6 times.

In another embodiment, the plant of the invention comprises 2.5, 2.6, 2.7, 2.8, 2.9, 3.0, 3.1, 3.2, 3.3, 3.4, 3.6, 3.8, 4.0, 4.2, 4.4, 4.6, 4.8, 5.0, 5.5, 6.0, 6.5, 7.0, 7.5, 8.0, 8.5, 9.0, 9.5, or 10.0 times the concentration and/or amount of Beta-Carotene compared to a control plant. In another embodiment, the plant of the invention comprises 1.2 times to 18 times the concentration and/or amount of Beta-Carotene compared to a control plant. In another embodiment, the plant of the invention comprises at 1.7 times the concentration and/or amount of Beta-Carotene compared to a control plant. In another embodiment, the plant of the invention comprise at least twice the concentration and/or amount of Beta-Carotene compared to a control plant. In another embodiment, the plant of the invention comprises at 2.5 times the concentration and/or amount of Beta-Carotene compared to a control plant. In another embodiment, the upper limit of the concentration and/or amount of Beta-Carotene in a plant of the invention compared to a control plant is 12 times. In another embodiment, the upper limit of the concentration and/or amount of Beta-Carotene in a plant of the invention compared to a control plant is 10 times. In another embodiment, the upper limit of the concentration and/or amount of Beta-Carotene in a plant of the invention compared to a control plant is 8 times.

In another embodiment, the carotenoid is Zeaxanthin. In another embodiment, the plant of the invention comprises 1.2 times to 25 times the concentration and/or amount of Zeaxanthin compared to a control plant. In another embodiment, the carotenoid is Zeaxanthin. In another embodiment, the plant of the invention comprises 10, 11, 12, 13, 14, 15, 16, 17, 18, 19, 20, 21, 22, 23, 24, 25, 26, 27, 28, 29, or 30 times the concentration and/or amount of Zeaxanthin compared to a control plant. In another embodiment, the plant of the invention comprises at least 10 times the concentration and/or amount of Zeaxanthin compared to a control plant. In another embodiment, the plant of the invention comprises at least twice the concentration and/or amount of Zeaxanthin compared to a control plant. In another embodiment, the plant of the invention comprises at least 12 times the concentration and/or amount of Zeaxanthin compared to a control plant. In another embodiment, the upper limit of the concentration and/or amount of Zeaxanthin in a plant of the invention compared to a control plant is 45 times. In another embodiment, the upper limit of the concentration and/or amount of Zeaxanthin in a plant of the invention compared to a control plant is 40 times. In another embodiment, the upper limit of the concentration and/or amount of Zeaxanthin in a plant of the invention compared to a control plant is 25 times.

In another embodiment, the carotenoid is Violaxanthin. In another embodiment, the plant of the invention comprises 1.2 times to 50 times the concentration and/or amount of Violaxanthin compared to a control plant. In another embodiment, the carotenoid is Violaxanthin. In another embodiment, the plant of the invention comprises 20 times to 50 times the concentration and/or amount of Violaxanthin compared to a control plant. In another embodiment, the carotenoid is Violaxanthin. In another embodiment, the plant of the invention comprises 15 times to 45 times the concentration and/or amount of Violaxanthin compared to a control plant. In another embodiment, the plant of the invention comprises 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 4, 5, 6, 8, 10, 12, 15, 20, 25, 30, 35, 40, 45, 50, 60 or 70 times the concentration and/or amount of Violaxanthin compared to a control plant.sss In another embodiment, the plant of the invention comprises at least 1.5 times the concentration and/or amount of Violaxanthin compared to a control plant. In another embodiment, the plant of the invention comprises at least 1.8 times the concentration and/or amount of Violaxanthin compared to a control plant. In another embodiment, the plant of the invention comprises at least twice the concentration and/or amount of Violaxanthin compared to a control plant. In another embodiment, the upper limit of the concentration and/or amount of Violaxanthin in a plant of the invention compared to a control plant is 12 times. In another embodiment, the upper limit of the concentration and/or amount of Violaxanthin in a plant of the invention compared to a control plant is 10 times. In another embodiment, the upper limit of the concentration and/or amount of Violaxanthin in a plant of the invention compared to a control plant is 8 times.

In another embodiment, the plant of the invention or its flower comprises from 0.2 to 20% Lutein of the total pigments and/or carotenoids content in a petal. In another embodiment, the plant of the invention or its flower comprises from 0.2 to 10% Lutein of the total pigments and/or carotenoids content in a petal. In another embodiment, the plant of the invention or its flower comprises from 0.5 to 5% w/w or v/v Lutein of the total pigments and/or carotenoids content in a petal. In another embodiment, the plant of the invention or its flower comprises from 0.5 to 4% Lutein of the total pigments and/or carotenoids content in a petal. In another embodiment, the plant of the invention or its flower comprises from 1 to 2% Lutein of the total pigments and/or carotenoids content in a petal. In another embodiment, the plant of the invention or its flower comprises from 1.1 to 1.8% Lutein of the total pigments and/or carotenoids content in a petal.

In another embodiment, the plant of the invention or its flower comprises from 20 to 50% w/w or v/v beta-Carotene of the total pigmentscontent in a petal. In another embodiment, the plant of the invention or its flower comprises from 25 to 50% w/w or v/v beta-Carotene of the total pigments content in a petal. In another embodiment, the plant of the invention or its flower comprises from 30 to 45% w/w or v/v beta-Carotene of the total pigments content in a petal. In another embodiment, the plant of the invention or its flower comprises from 35 to 45% w/w or v/v beta-Carotene of the total pigments content in a petal. In another embodiment, the plant of the invention or its flower comprises from 39 to 45% w/w or v/v beta-Carotene of the total carotenoid content in a petal.

In another embodiment, the plant of the invention or its flower comprises from 10 to 40% w/w or v/v chlorophyll A of the total pigments content in a petal. In another embodiment, the plant of the invention or its flower comprises from 15 to 40% w/w or v/v chlorophyll A of the total pigmentscontent in a, petal. In another embodiment, the plant of the invention or its flower comprises from 20 to 35% w/w or v/v chlorophyll A of the total pigments content in a petal. In another embodiment, the plant of the invention or its flower comprises from 22 to 30% w/w or v/v chlorophyll A of the total pigments content in a petal. In another embodiment, the plant of the invention or its flower comprises from 22 to 28% w/w or v/v chlorophyll A of the total pigments content in a petal.

In another embodiment, the plant of the invention or its flower comprises from 5 to 25% w/w or v/v chlorophyll B of the total pigments and/or carotenoids content in a petal.

In another embodiment, the plant of the invention or its flower comprises from 5 to 20% w/w or v/v chlorophyll B of the total pigments and/or carotenoids content in a petal. In another embodiment, the plant of the invention or its flower comprises from 8 to 15% w/w or v/v chlorophyll B of the total pigments and/or carotenoids content in a petal. In another embodiment, the plant of the invention or its flower comprises from 9 to 14% w/w or v/v chlorophyll B of the total pigments and/or carotenoids content in a petal.

In another embodiment, the plant of the invention or its flower comprises from 5 to 40% w/w or v/v alpha-Tocopherol of the total pigments and/or carotenoids content in a petal. In another embodiment, the plant of the invention or its flower comprises from 5 to 30% w/w or v/v alpha-Tocopherol of the total pigments and/or carotenoids content in a petal. In another embodiment, the plant of the invention or its flower comprises from 8 to 30% w/w or v/v alpha-Tocopherol of the total pigments and/or carotenoids content in a petal. In another embodiment, the plant of the invention or its flower comprises from 9 to 27% w/w or v/v alpha-Tocopherol of the total pigments and/or carotenoids content in a petal.

In another embodiment, at least 5% of a petal's surface area of a flower or a flower's surface area having an altered phenotype (a plant of the invention) is green, yellow, and/or orange. In another embodiment, at least 7.5% of a petal's surface area of a flower or a flower's surface area having an altered phenotype (a plant of the invention) is green, yellow, and/or orange. In another embodiment, at least 10%, 15%, 20%, 25%, 30%, 35%, 40%, 45%, 0r 50% of a petal's surface area of a flower or a flower's surface area having an altered phenotype (a plant of the invention) is green, yellow, and/or orange. In another embodiment, at least 15%, 20%, 25%, 30%, 35%, 40%, 45%, or 50% of a petal's surface area of a flower or a flower's surface area having an altered phenotype (a plant of the invention) is not white. In another embodiment, at least 12% of a petal's surface area of a flower or a flower's surface area having an altered phenotype (a plant of the invention) is green, yellow, and/or orange. In another embodiment, at least 13% of a petal's surface area of a flower or a flower's surface area having an altered phenotype (a plant of the invention) is green, yellow, and/or orange. In another embodiment, at least 15% of a petal's surface area of a flower or a flower's surface area having an altered phenotype (a plant of the invention) is green, yellow, and/or orange. In another embodiment, at least 20% of a petal's surface area of a flower or a flower's surface area having an altered phenotype (a plant of the invention) is green, yellow, and/or orange. In another embodiment, at least 25% of a petal's surface area of a flower or a flower's surface area having an altered phenotype (a plant of the invention) is green, yellow, and/or orange. In another embodiment, at least 30% of a petal's surface area of a flower or a flower's surface area having an altered phenotype (a plant of the invention) is green, yellow, and/or orange. In another embodiment, at least 40% of a petal's surface area of a flower or a flower's surface area having an altered phenotype (a plant of the invention) is green, yellow, and/or orange. In another embodiment, 10% to 99% of a petal's surface area of a flower or a flower's surface area having an altered phenotype (a plant of the invention) is green, yellow, and/or orange. In another embodiment, 20% to 70% of a petal's surface area of a flower or a flower's surface area having an altered phenotype (a plant of the invention) is green, yellow, and/or orange. In another embodiment, 40% to 80% of a petal's surface area of a flower or a flower's surface area having an altered phenotype (a plant of the invention) is green, yellow, and/or orange. In another embodiment, "a petal" includes petals or all petals within a single flower. In another embodiment, "a flower's surface area" is the entire surface area of all petals within a single flower. In another embodiment, "a flower's surface area" is the entire surface area of all petals within all flowers within a single plant of the invention.

In another embodiment, at least 5% of a petal's surface area of a flower or a flower's surface area having an altered phenotype (a plant of the invention) is white. In another embodiment, at least 7.5% of a petal's surface area of a flower or a flower's surface area having an altered phenotype (a plant of the invention) is white. In another embodiment, at least 10% of a petal's surface area of a flower or a flower's surface area having an altered phenotype (a plant of the invention) is white. In another embodiment, at least 12% of a petal's surface area of a flower or a flower's surface area having an altered phenotype (a plant of the invention) is white. In another embodiment, at least 13% of a petal's surface area of a flower or a flower's surface area having an altered phenotype (a plant of the invention) is white. In another embodiment, at least 15% of a petal's surface area of a flower or a flower's surface area having an altered phenotype (a plant of the invention) is white. In another embodiment, at least 20% of a petal's surface area of a flower or a flower's surface area having an altered phenotype (a plant of the invention) is white. In another embodiment, at least 25% of a petal's surface area of a flower or a flower's surface area having an altered phenotype (a plant of the invention) is white. In another embodiment, at least 30% of a petal's surface area of a flower or a flower's surface area having an altered phenotype (a plant of the invention) is white. In another embodiment, at least 40% of a petal's surface area of a flower or a flower's surface area having an altered phenotype (a plant of the invention) is white. In another embodiment, 10% to 99% of a petal's surface area of a flower or a flower's surface area having an altered phenotype (a plant of the invention) is white. In another embodiment, 10% to 70% of a petal's surface area of a flower or a flower's surface area having an altered phenotype (a plant of the invention) is white. In another embodiment, 20% to 50% of a petal's surface area of a flower or a flower's surface area having an altered phenotype (a plant of the invention) is white. In another embodiment, 10% to 30% of a petal's surface area of a flower or a flower's surface area having an altered phenotype (a plant of the invention) is white. In another embodiment, at least 5% of a petal's surface area of a flower or a flower's surface area having an altered phenotype (a plant of the invention) is yellow.

In another embodiment, the present invention provides a method for screening and/or selecting and/or identifying a *Gypsophila* plant for its ability to produce progeny and/or offspring having an altered flower phenotype, wherein the flower having an altered phenotype comprises an elevated concentration and/or amount of chlorophyll A, chlorophyll B, xanthophyll, a carotenoid, a pigment, Lutein, Beta-Carotene, Antheraxanthin, zeaxanthin, Violaxanthin, or any combination thereof, wherein the elevated amount of: chlorophyll A, chlorophyll B, xanthophyll, a carotenoid, a pigment, Lutein, Beta-Carotene, Antheraxanthin, zeaxanthin, Violaxanthin, or any combination thereof, is at least 1.2 times the concentration and/or amount of: chlorophyll A, chlorophyll B, xanthophyll, a carotenoid, a pigment, Lutein, Beta-Carotene, Antheraxanthin, zeaxanthin, Violaxanthin, or any combination thereof in a control plant or control *Gypsophila* (such as defined herein), comprising: (a) preparing cut flowers from the individual plant; and (b) contacting each cut flower from a *Gypsophila* plant with a composition comprising an aqueous solution and 10 to 100 mg/l Gibberellic acid (GA) for at least one days or at least two days, wherein a flower developing petals having cream color and/or yellow color as oppose to white is selected and/or identified as having an altered phenotype and/or comprising an elevated concentration and/or amount of chlorophyll A, chlorophyll B, xanthophyll, a carotenoid, a pigment, Lutein, Beta-Carotene, Antheraxanthin, zeaxanthin, Violaxanthin, or any combination thereof.

In another embodiment, an offspring of the parent plant selected by the methods described herein is a direct progeny of the parent plant (F1 generation). In another embodiment, an offspring of the parent plant is produced sexually or asexually. In another embodiment, an offspring is the derived from a plant or plants having elevated amount of: a chlorophyll, a pigment, a carotenoid, or any combination thereof (produced sexually or asexually). In another embodiment, an offspring of the parent plant selected by the methods described herein is obtained by further crossings of the direct progeny offsprings (crossing of F1 also referred to as indirect offspring of P (parent)). In another embodiment, a plant having an altered flower phenotype is a result of 2 to 50 crossings of offspring stemming from the parent plant. In another embodiment, a plant having an altered flower phenotype is a result of 2 to 10 crossings of offspring stemming from the parent plant. In another embodiment, a plant having an altered flower phenotype is a result of 20 to 50 crossings of offspring stemming from the parent plant. In another embodiment, a plant having an altered flower phenotype is a result of 12 to 30 crossings of offspring stemming from the parent plant. In another embodiment, a plant having an altered flower phenotype is a result of 5 to 25 crossings of offspring stemming from the parent plant.

In another embodiment, a plant having an altered flower phenotype is the $2^{nd}$ to $50^{th}$ generation of the P (parent). In another embodiment, a plant having an altered flower phenotype obtained in the $2^{nd}$ to $50^{th}$ generation of the P (parent) is referred to as an indirect offspring. In another embodiment, an indirect offspring is the product of propagation or sexual reproduction stemming or derived from a plant or plants having elevated amount of: chlorophyll, a pigment, a carotenoid, or any combination thereof. In another embodiment, an indirect offspring is the product of propagation or sexual reproduction stemming or derived from a plant or plants of the invention which is/are not a parent/parents plant.

In another embodiment, an offspring is a plant produced directly or indirectly from a plant of the invention. In another embodiment, an offspring is a plant produced directly or indirectly from a parent *Gypsophila* plant of the invention. In another embodiment, an offspring is a plant produced directly or indirectly from a *Gypsophila* plant having an altered flower phenotype as described herein. In another embodiment, an offspring is F1 to F100,000 of a parent *Gypsophila* plant of the invention. In another embodiment, an offspring is F1 to F100,000 of a *Gypsophila* plant having an altered flower phenotype as described herein. In another embodiment, an offspring is F1 to F1000 of a *Gypsophila* plant having an altered flower phenotype as described herein. In another embodiment, an offspring is F1 to F50 of a *Gypsophila* plant having an altered flower phenotype as described herein.

In another embodiment, an offspring is an asexual offspring of the parent plant. In another embodiment, an offspring is an asexual offspring of a plant of the invention. In another embodiment, an offspring is a vegetative offspring of the parent plant. In another embodiment, an offspring is a vegetative offspring of a plant of the invention. In another embodiment, an offspring is an asexual offspring of another offspring that was sexually produced. In another embodiment, an offspring or a plant of the invention is produced by vegetative propagation or propagation. In another embodiment, an offspring is a propagation product of the parent. In another embodiment, a plant of the invention or a part of a plant of the invention is a propagation product of the parent plant. In another embodiment, an offspring is a propagation product of the parent. In another embodiment, a plant of the invention or a part of a plant of the invention is a clonal propagation product of the parent plant. In another embodiment, a plant of the invention or a part of a plant of the invention is also a propagation product of the plant of the invention. In another embodiment, a plant of the invention is any propagation product that was derived from a parent plant or a plant described herein. In another embodiment, a plant of the invention is a clonal propagation product that was derived from a parent plant or a plant described herein.

In another embodiment, the present invention provides a method for screening and/or selecting and/or identifying a *Gypsophila* parent plant capable of producing a *Gypsophila* offspring plant, wherein the *Gypsophila* offspring plant is characterized by an altered flower phenotype, wherein the flower having an altered phenotype comprises an elevated concentration and/or amount of chlorophyll A, chlorophyll B, xanthophyll, a carotenoid, a pigment, Lutein, Beta-Carotene, Antheraxanthin, zeaxanthin, Violaxanthin, or any combination thereof, wherein the elevated amount of: chlorophyll A, chlorophyll B, xanthophyll, a carotenoid, a pigment, Lutein, Beta-Carotene, Antheraxanthin, zeaxanthin, Violaxanthin, or any combination thereof, is at least 1.2 times the concentration and/or amount of: chlorophyll A, chlorophyll B, xanthophyll, a carotenoid, a pigment, Lutein, Beta-Carotene, Antheraxanthin, zeaxanthin, Violaxanthin, or any combination thereof in a control plant or control *Gypsophila* (such as defined herein), comprising: (a) preparing cut flowers from the individual plant; and (b) contacting each cut flower from a *Gypsophila* plant with a composition comprising an aqueous solution and 10 to 100 mg/l Gibberellic acid (GA) (selection composition) for at least one days, wherein a flower developing petals having cream and/or yellow color as oppose to white is selected and/or identified as having an altered phenotype and/or comprising an elevated concentration and/or amount of chlorophyll A, chlorophyll B, xanthophyll, a carotenoid, a pigment, Lutein, Beta-Carotene, Antheraxanthin, zeaxanthin, Violaxanthin, or any combination thereof.

In another embodiment, the present invention provides a method for screening, selecting, identifying or any combination thereof of a population of *Gypsophila* plants for a parent generation of *Gypsophila* plants capable of producing an offspring plant having a flower with an altered phenotype, wherein a flower having an altered phenotype comprises an elevated amount of chlorophyll A, wherein the elevated amount of chlorophyll A is at least 1.2 times the concentration of chlorophyll A compared to the concentration of chlorophyll A in a control *Gypsophila*, comprising: (a) preparing cut flowers from the individual parent generation of *Gypsophila* plants; and (b) contacting each cut flower from said individual parent generation of *Gypsophila* plants with a composition comprising water, 10 to 50 mg/I Gibberellic acid, and 5 to 20 mg/l benzyl adenine, for at least 2 days, wherein a flower developing petals having yellow color, cream color or any combination thereof, as oppose to white is selected as a parent generation for *Gypsophila* plants capable of producing an offspring plant having a flower with an altered phenotype.

In another embodiment, the present invention provides a method for screening a population of *Gypsophila* plants for the presence therein of an individual plant having an altered flower phenotype, wherein the flower having an altered phenotype comprises at least 1.2 times the amount and/or the concentration of a carotenoid and/or a pigment compared to the amount and/or the concentration of the same carotenoid and/or the same pigment in a control plant (control *Gypsophila* flower), comprising: (a) preparing cut flowers from the individual plant; and (b) contacting each cut flower with a composition comprising an aqueous solution and 5 to 80 mg/l Gibberellic acid for at least a day, wherein a flower developing petals having cream and/or yellow color, as oppose to white is selected and/or identified as having an altered flower phenotype. In another embodiment, a method for screening is a method for selecting.

In another embodiment, the present invention provides a method for screening a population of *Gypsophila* parent plant capable of producing an offspring plant having an altered flower phenotype, wherein the flower having an altered phenotype comprises at least 1.2 times the amount and/or the concentration of a carotenoid and/or a pigment compared to the amount and/or the concentration of the same carotenoid and/or the same pigment in a control plant (control *Gypsophila* flower), comprising: (a) preparing cut flowers from a library of *Gypsophila* plants; and (b) contacting each cut flower with a composition comprising an aqueous solution and 5 to 80 mg/l Gibberellic acid for at least a day, wherein a flower developing petals having cream and/or yellow color as oppose to white is selected and/or identified as a parent plant capable of producing an offspring plant having an altered flower phenotype. In another embodiment, a method for screening is a method for selecting.

In another embodiment, *Gypsophila* parent plants capable of producing an offspring plant having an altered flower phenotype do not have an altered flower phenotype. In another embodiment, *Gypsophila* parent plants capable of producing an offspring plant having an altered flower phenotype can be identified with the compositions as described herein.

In another embodiment, having an altered flower phenotype comprises the presence of an elevated (at least 1.2 times compared to control plant) concentration and/or amount of chlorophyll A, chlorophyll B, xanthophyll, a carotenoid, a pigment, Lutein, Beta-Carotene, Antheraxanthin, zeaxanthin, Violaxanthin, or any combination thereof within the plant. In another embodiment, having an altered flower phenotype comprises the presence of an elevated (at least 1.2 times compared to control plant) concentration and/or amount of chlorophyll A, chlorophyll B, xanthophyll, a carotenoid, a pigment, Lutein, Beta-Carotene, Antheraxanthin, zeaxanthin, Violaxanthin, or any combination thereof within the plant's flower or within a petal.

In another embodiment, having an altered flower phenotype is further characterized by the presence of 15 to 70% Lutein of the total carotenoid content in a petal or a flower. In another embodiment, having an altered flower phenotype is further characterized by the presence of 25 to 50% Lutein of the total carotenoid content in a petal or a flower. In another embodiment, having an altered flower phenotype is further characterized by the presence of 25 to 35% Lutein from the total carotenoid content in a petal or a flower.

In another embodiment, having an altered flower phenotype is further characterized by the presence of 10 to 55% Beta-Carotene from the total carotenoid content in a petal or a flower. In another embodiment, having an altered flower phenotype is further characterized by the presence of 20 to 45% Beta-Carotene from the total carotenoid content in a petal or a flower. In another embodiment, having an altered flower phenotype is further characterized by the presence of 20 to 35% Beta-Carotene from the total carotenoid content in a petal or a flower. In another embodiment, having an altered flower phenotype is further characterized by the presence of 25 to 50% Beta-Carotene from the total carotenoid content in a petal or a flower. In another embodiment, having an altered flower phenotype is further characterized by the presence of 20 to 30% Beta-Carotene from the total carotenoid content in a petal or a flower.

In another embodiment, having an altered flower phenotype is further characterized by petals having green, yellow, and/or orange color in at least 5% of a petal's surface area or a flower's surface area. In another embodiment, having an altered flower phenotype is further characterized by petals having green, yellow, and/or orange color in at least 7% of a petal'S surface area or a flower's surface area. In another embodiment, having an altered flower phenotype is further characterized by petals having green, yellow, and/or orange color in at least 10% of a petal's surface area or a flower's surface area. In another embodiment, having an altered flower phenotype is further characterized by petals having green, yellow, and/or orange color in at least 20% of a petal's surface area or a flower's surface area. In another embodiment, having an altered flower phenotype is further characterized by petals having green, yellow, and/or orange color in at least 30% of a petal's surface area or a flower's surface area. In another embodiment, having an altered flower phenotype is further characterized by petals having green, yellow, and/or orange color in at least 40% of a petal's surface area or a flower's surface area.

In another embodiment, having an altered flower phenotype is further characterized by petals having green, yellow, and/or orange color in 10% to 100% of a petal's surface area or a flower's surface area. In another embodiment, having an altered flower phenotype is further characterized by petals having green, yellow, and/or orange color in 40% to 100% of a petal's surface area or a flower's surface area. In another embodiment, having an altered flower phenotype is further characterized by petals having green, yellow, and/or orange color in 20% to 80% of a petal's surface area or a flower's surface area. In another embodiment, having an altered flower phenotype is further characterized by petals having green, yellow, and/or orange color in 50% to 100% of a petal's surface area or a flower's surface area. In another embodiment, having an altered flower phenotype is further characterized by petals having green, yellow, and/or orange color in 75% to 100% of a petal's surface area or a flower's surface area. In another embodiment, having an altered flower phenotype is further characterized by petals having green, yellow, and/or orange color in 85% to 100% of a petal's surface area or a flower's surface area. In another embodiment, having an altered flower phenotype is further characterized by petals having green, yellow, and/or orange color in 40% to 90% of a petal's surface area or a flower's surface area. In another embodiment, having an altered flower phenotype is further characterized by petals having green, yellow, and/or orange color in 50% to 90% of a petal's surface area or a flower's surface area.

In another embodiment, having an altered flower phenotype is further characterized by petals having white color in at least 2.5% of a petal's surface area or a flower's surface area. In another embodiment, having an altered flower phenotype is further characterized by petals having white color in at least 5% of a petal's surface area or a flower's surface area. In another embodiment, having an altered flower phenotype is further characterized by petals having white color in at least 7% of a petal's surface area or a flower's surface area. In another embodiment, having an altered flower phenotype is further characterized by petals having white color in at least 15% of a petal's surface area or a flower's surface area. In another embodiment, having an altered flower phenotype is further characterized by petals having white color in at least 20% of a petal's surface area or a flower's surface area. In another embodiment, having an altered flower phenotype is further characterized by petals having white color in at least 30% of a petal's surface area or a flower's surface area.

In another embodiment, having an altered flower phenotype is further characterized by petals having white color in 2.5% to 80% of a petal's surface area or a flower's surface area. In another embodiment, having an altered flower phenotype is further characterized by petals having white color in 2.5% to 50% of a petal's surface area or a flower's surface area. In another embodiment, having an altered flower phenotype is further characterized by petals having white color in 5% to 40% of a petal's surface area or a flower's surface area. In another embodiment, having an altered flower phenotype is further characterized by petals having white color in 5% to 40% of a petal's surface area or a flower's surface area. In another embodiment, having an altered flower phenotype is further characterized by petals having white color in 10% to 30% of a petal's surface area or a flower's surface area.

In another embodiment, having an altered flower phenotype is further characterized by petals having white color in 85% to 100% of a petal's surface area or a flower's surface area. In another embodiment, having an altered flower phenotype is further characterized by petals having green, yellow, and/or orange color in 40% to 90% of a petal's surface area or a flower's surface area. In another embodiment, having an altered flower phenotype is further characterized by petals having green, yellow, and/or orange color in 50% to 90% of a petal's surface area or a flower's surface area.

In another embodiment, at least 1.2 times is at least 1.4 times. In another embodiment, at least 1.2 times is at least 1.5 times. In another embodiment, at least 1.2 times is at least 1.8 times. In another embodiment, at least 1.2 times is at least twice. In another embodiment, at least 1.2 times is at least 2.5 times. In another embodiment, at least 1.2 times is at least 2.8 times. In another embodiment, at least 1.2 times is at least 3 times. In another embodiment, at least 1.2 times is at least 3.5 times. In another embodiment, at least 1.2 times is at least 4 times. In another embodiment, at least 1.2 times is at least 4.5 times. In another embodiment, at least 1.2 times is at least 5 times.

In another embodiment, at least 1.2 times is between 1.2 to 20 times. In another embodiment, at least 1.2 times is between 1.2 to 18 times. In another embodiment, at least 1.2 times is between 1.5 to 20 times. In another embodiment, at least 1.2 times is between 1.2 to 15 times. In another embodiment, at least 1.2 times is between 1.2 to 12 times. In another embodiment, at least 1.2 times is between 1.5 to 10 times. In another embodiment, at least 1.2 times is between 2 to 10 times. In another embodiment, at least 1.2 times is between 1.5 to 8 times.

In another embodiment, a composition of the invention comprises an aqueous solution comprises water and 10 to 100 mg/l Gibberellic acid. In another embodiment, a composition comprising an aqueous solution comprises water and 10 to 100 mg/l Gibberellic acid. In another embodiment, a composition comprising an aqueous solution comprises water and 12 to 50 mg/l Gibberellic acid. In another embodiment, a composition comprising an aqueous solution comprises water and 10 to 30 mg/l Gibberellic acid. In another embodiment, a composition comprising an aqueous solution comprises water and 20 to 50 mg/l Gibberellic acid. In another embodiment, a composition comprising an aqueous solution comprises water and 15 to 50 mg/l Gibberellic acid.

In another embodiment, a composition comprising an aqueous solution as described herein further comprises 1 to 100 mg/l benzyl adenine. In another embodiment, a composition comprising an aqueous solution as described herein further comprises 5 to 80 mg/l benzyl adenine. In another embodiment, a composition comprising an aqueous solution as described herein further comprises 5 to 50 mg/l benzyl adenine. In another embodiment, a composition comprising an aqueous solution as described herein further comprises 5 to 20 mg/l benzyl adenine. In another embodiment, a composition comprising an aqueous solution as described herein further comprises 10 to 25 mg/l benzyl adenine. In another embodiment, a composition comprising an aqueous solution as described herein further comprises 15 to 45 mg/l benzyl adenine.

In another embodiment, the phrase "for at least a day" is at least 30 hours. In another embodiment, the phrase "for at least a day" is at least 2 days. In another embodiment, the phrase "for at least a day" is at least 3 days. In another embodiment, the phrase "for at least a day" is at least 4 days. In another embodiment, the phrase "for at least a day" is at least 5 days. In another embodiment, the phrase "for at least a day" is from one day to 10 days. In another embodiment, the phrase "for at least a day" is from one day to 7 days. In another embodiment, the phrase "for at least a day" is from 2 days to 10 days. In another embodiment, the phrase "for at least a day" is from 2 days to 5 days. In another embodiment, the phrase "for at least a day" is from 3 days to 7 days.

In another embodiment, the present invention provides a plant or an offspring of a parent-plant or parents-plants as described herein characterized as comprising an elevated concentration and/or amount of chlorophyll A, chlorophyll B, xanthophyll, a carotenoid, a pigment, Lutein, Beta-Carotene, Antheraxanthin, zeaxanthin, Violaxanthin, or any combination thereof, wherein the elevated amount of: chlorophyll A, chlorophyll B, xanthophyll, a carotenoid, a pigment, Lutein, Beta-Carotene, Antheraxanthin, zeaxanthin, Violaxanthin, or any combination thereof, is at least 1.2 times the concentration and/or amount of: chlorophyll A, chlorophyll B, xanthophyll, a carotenoid, a pigment, Lutein, Beta-Carotene, Antheraxanthin, zeaxanthin, Violaxanthin, or any combination thereof in a control plant or control *Gypsophila* (such as defined herein). As described herein, the presence of an elevated (at least 1.2 times compared to control plant) concentration and/or amount of chlorophyll A, chlorophyll B, xanthophyll, a carotenoid, a pigment, Lutein, Beta-Carotene, Antheraxanthin, zeaxanthin, Violaxanthin, or any combination thereof within the plant or within a plant's flower. In another embodiment, "a plant's flower" includes a petal or petals with a flower.

In another embodiment, an offspring is a plant derived and/or produced by or from a plant of the invention. In another embodiment, an offspring is a plant part derived from a plant of the invention. In another embodiment, an offspring is a plant wherein its ancestor, its parent or its "P-generation" is a plant of the invention. In another embodiment, an offspring is in the form of a twig. In another embodiment, an offspring or a plant part is in the form of a shoot. In another embodiment, an offspring or a plant part is in the form of a slip. In another embodiment, an offspring or a plant part is in the form of a cutting. In another embodiment, an offspring or a plant part is in the form of a seed.

In another embodiment, "plant part" is any part or an organ of a plant described herein. In another embodiment, "a part of an offspring" is any part or an organ of an offspring of a plant as described herein. In another embodiment, a plant is a "plant part".

In another embodiment, the plant and/or the offspring is a *Gypsophila* having altered phenotype and favorable characteristics as described herein. In another embodiment, the plant and/or the offspring is further characterized by the presence of 15 to 70% Lutein of the total carotenoid content in a petal. In another embodiment, the plant and/or the offspring is further characterized by the presence of 25 to 50% Lutein of the total carotenoid content in a petal. In another embodiment, the plant and/or the offspring is further characterized by the presence of 25 to 35% Lutein from the total carotenoid content in a petal.

In another embodiment, the plant and/or the offspring is further characterized by the presence of 10 to 55% Beta-Carotene from the total carotenoid content in a petal or a flower. the plant and/or the offspring is further characterized by the presence of 20 to 45% Beta-Carotene from the total carotenoid content in a petal or a flower. In another embodiment, the plant and/or the offspring is further characterized by the presence of 20 to 35% Beta-Carotene from the total carotenoid content in a petal or a flower. In another embodiment, the plant and/or the offspring is further characterized by the presence of 25 to 50% Beta-Carotene from the total carotenoid content in a petal or a flower. In another embodiment, the plant and/or the offspring is further characterized by the presence of 20 to 30% Beta-Carotene from the total carotenoid content in a petal or a flower.

In another embodiment, the plant and/or the offspring is further characterized by petals having green, yellow, and/or orange color in at least 5% of a petal's surface area or a flower's surface area. In another embodiment, the plant and/or the offspring is further characterized by petals having green, yellow, and/or orange color in at least 7% of a petal's surface area or a flower's surface area. In another embodiment, the plant and/or the offspring is further characterized by petals having green, yellow, and/or orange color in at least 10% of a petal's surface area or a flower's surface area. In another embodiment, the plant and/or the offspring is further characterized by petals having green, yellow, and/or orange color in at least 20% of a petal's surface area or a flower's surface area. In another embodiment, the plant and/or the offspring is further characterized by petals having green, yellow, and/or orange color in at least 30% of a petal's surface area or a flower's surface area. In another embodiment, the plant and/or the offspring is further characterized by petals having green, yellow, and/or orange color in at least 40% of a petal's surface area or a flower's surface area.

In another embodiment, the plant and/or the offspring is further characterized by petals having green, yellow, and/or orange color in 10% to 100% of a petal's surface area or a flower's surface area. In another embodiment, the plant and/or the offspring is further characterized by petals having green, yellow, and/or orange color in 40% to 100% of a petal's surface area or a flower's surface area. In another embodiment, the plant and/or the offspring is further characterized by petals having green, yellow, and/or orange color in 20% to 80% of a petal's surface area or a flower's surface area. In another embodiment, the plant and/or the offspring is further characterized by petals having green, yellow, and/or orange color in 50% to 100% of a petal's surface area or a flower's surface area. In another embodiment, the plant and/or the offspring is further characterized by petals having green, yellow, and/or orange color in 75% to 100% of a petal's surface area or a flower's surface area. In another embodiment, the plant and/or the offspring is further characterized by petals having green, yellow, and/or orange color in 85% to 100% of a petal's surface area or a flower's surface area. In another embodiment, the plant and/or the offspring is further characterized by petals having green, yellow, and/or orange color in 40% to 90% of a petal's surface area or a flower's surface area. In another embodiment, the plant and/or the offspring is further characterized by petals having green, yellow, and/or orange color in 50% to 90% of a petal's surface area or a flower's surface area.

In another embodiment, the plant and/or the offspring is further characterized by petals having white color in at least 2.5% of a petal's surface area. In another embodiment, the plant and/or the offspring is further characterized by petals having white color in at least 5% of a petal's surface area. In another embodiment, the plant and/or the offspring is further characterized by petals having white color in at least 7% of a petal's surface area. In another embodiment, the plant and/or the offspring is further characterized by petals having white color in at least 15% of a petal's surface area. In another embodiment, the plant and/or the offspring is further characterized by petals having white color in at least 20% of a petal's surface area. In another embodiment, the plant and/or the offspring is further characterized by petals having white color in at least 30% of a petal's surface area.

In another embodiment, the plant and/or the offspring is further characterized by petals having white color in 2.5% to 80% of a petal's surface area. In another embodiment, the plant and/or the offspring is further characterized by petals having white color in 2.5% to 50% of a petal's surface area. In another embodiment, the plant and/or the offspring is further characterized by petals having white color in 5% to 40% of a petal's surface area. In another embodiment, the plant and/or the offspring is further characterized by petals having white color in 5% to 40% of a petal's surface area. In another embodiment, the plant and/or the offspring is further characterized by petals having white color and/or yellow in 10% to 30% of a petal 'surface area.

In another embodiment, a plant of the invention is a direct offspring of a parent that will only develop petals having green, yellow, and/or cream color upon contacting the flower with an aqueous composition comprising 10 to 50 mg/l Gibberellic acid for at least a day as described hereinabove.

In another embodiment, the invention further provides an aqueous composition comprising: 10 to 50 mg/l Gibberellic acid as further described herein. In another embodiment, the invention further provides that the aqueous composition comprising: 10 to 50 mg/l Gibberellic acid is for selecting a plant having elevated amount of chlorophyll A. another embodiment, the invention further provides an aqueous composition comprising: 10 to 50 mg/l Gibberellic is a selecting composition for plants having an elevated amount of a pigment/s and/or carotenoid/s. In another embodiment, the aqueous composition is used for identifying and/or selecting a parent plant as described herein.

In another embodiment, petals having yellow/green/orange color are petals having yellow/green/orange color in 2% to 100% of a petal's surface area. In another embodiment, petals having yellow/green/orange color are petals having yellow/green/orange color in 2% to 100% of a petal's surface area at anthesis or at the closed bud phase. In another embodiment, petals having yellow/green/orange color are petals having yellow/green/orange color in 2% to 80% of a petal's surface area. In another embodiment, petals having yellow/green/orange color are petals having yellow/green/orange color in 5% to 75% of a petal's surface area. In another embodiment, petals having yellow/green/orange color are petals having yellow/green/orange color in 10% to 50% of a petal's surface area. In another embodiment, petals having yellow/green/orange color are petals having yellow/green/orange color in 20% to 70% of a petal's surface area.

In another embodiment, a flower at the closed bud phase has a dormant bud. In another embodiment, a flower at the closed bud phase has a tight bud. In another embodiment, a flower at the closed bud phase is at the bud swell phase. In another embodiment, a flower at the closed bud phase comprises an early green tip. In another embodiment, the closed bud phase is prior to the bud break phase. In another embodiment, the closed bud phase is prior to the bud burst phase.

In another embodiment, a flower is a Semi-Double which is a flower with more than one row of petals, and a clearly defined central which is visible. In another embodiment, a flower type is a double which is a flower with a few rows of petals, and a central which is not visible. In another embodiment, a flower is a double multi-flowers which is a flower with a few rows of petals, a central which is not visible and developing young buds located at the flower center. In another embodiment, a flower is smaller than 4 mm (diameter). In another embodiment, a flower is smaller than 5 mm (diameter). In another embodiment, a flower is 2 mm to 10 mm (diameter). In another embodiment, a flower is 4 mm to 10 mm (diameter). In another embodiment, a flower has a diameter of 4 to 8 mm. In another embodiment, a flower is 4 mm to 18 mm (diameter). In another embodiment, a flower is 6 mm to 15 mm (diameter).

In some embodiments, the invention is based on the unexpected discovery of the composition of the invention that can differentiate between plants of the invention and/or parent plants and control plants. These essential traits within the parent plant (petals having yellow/light yellow/cream color within the parent plant) cannot be detected with a naked eye without contacting a cut flower or a cutting with a selecting composition as described herein.

As used herein, the singular forms "a", "an", and "the" include plural forms unless the context clearly dictates otherwise. Thus, for example, reference to "a therapeutic agent" includes reference to more than one therapeutic agent.

Unless specifically stated or obvious from context, as used herein, the term "or" is understood to be inclusive.

The term "including" is used herein to mean, and is used interchangeably with, the phrase "including but not limited to".

In one embodiment, the terms "comprises," "comprising," "containing," "having" and the like can have the meaning ascribed to them in U.S. patent law and can mean "includes," "including," and the like; "consisting essentially of or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments. In another embodiment, the term "comprise" includes the term "consist".

In another embodiment, any recitation of "%" is weight/weight %, volume/volume % or weight/volume %.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Deposit Information

A deposit of seeds of *Gypsophilia paniculata* DGYPGRNGYP disclosed above and recited in the claims, has been made with the NCIMB Ltd. Ferguson Building, Craibstone Estate, Bucksburn, Aberdeen, AV21 9YA Scotland on Aug. 14, 2020. The accession number for those deposited seeds is NCIMB 43656. Upon issuance of a patent, all restrictions upon the deposits will be removed, and the deposits are intended to meet all of the requirements of 37 C.F.R. § 1.801-1.809. The deposit[s] has been accepted under the Budapest Treaty and will be maintained in the depository for a period of 30 years, or 5 years after the last request, or for the effective life of the patent, whichever is longer, and will be replaced if necessary during that period.

EXAMPLES

Definitions

Flower type: single: a flower with one row of petals Semi-Double: a flower with more than one row of petals, and a clearly defined central which is visible. Double: a flower with a few rows of petals, and a central which is not visible. Double Multi-flowers: a flower with a few rows of petals, a central which is not visible and developing young buds are seen at the flower center.

Flower size: Small—smaller than 5 mm, Medium—between 6 to 9 mm, Large—between 9 to 12 mm. XL—larger than 12 mm.

Flower development stage: 1—closed flower bud, 2—flower before anthesis, 3—flower at anthesis.

Example 1

*G. paniculaca* Carotenoids/Pigments and Shelf-Life Selection Strategies

Endeavor to merge particular color pattern traits with other desirable polygenic characteristics in *G. paniculaca* have been excruciatingly slow and laborious. As described herein, however, the inventors have derived a novel flower color and or flower color pattern.

Origin and Breeding History of the Green Petals Trait in *Gypsophila*

The crossing and selections that led directly to *Gypsophila* plants having green petals was done according to the following description.

Vase life evaluation of stems was done routinely in the process of selecting new varieties of cut flowers. Preservative solutions are generally required to supply energy source, reduce microbial build up and vascular blockage, increase water uptake of the stem, and arrest the negative effect of ethylene (Nigussie, 2005). Incorporation of different chemical preservatives to the holding (vase) solution is recommended to prolong the vase life of cut flowers (Ichimura et al., 2006). Thus, alternative techniques for extending the vase life of cut flowers are commercial interest (Serek et al. 1995).

In February 2006, in a different experiment for prolonging the effective period of cut flowers, the researchers increased the common GA concentration from 5 mg/l to 10 mg/l and up to 25 mg/l and also added 10 mg/l BA (benzyl adenine) to the solution. Unexpectedly, under the condition of the new flower cut solution (also described as selecting composition) a new variety was discovered—a plant having cream and/or light yellow petals. However, 2 days of incubating a variety of flower cuts from various plants in this new selecting/selection composition revealed that a very low fraction of the population is developing green/yellow/cream petals—this variety was selected as parent plants. Plant 4016 was found in a F1 hybrid population of white *Gypsophila* breeding line derived from open and self-pollinations.

Selection for green and/or yellow flower colors was first made in populations arising from open and self-pollinations of 4016, as the female plant. After several generations between 2006 and 2010, these selections resulted in 8 lines that were noted as 5209, 5210, 5211, 5212, 5213 and 5453.

Plants 5209 and 5210 were selected in 2009, 5209 was characterized by double flower of cream—light green color (at anthesis), 5210 was characterized by double flower of greenish color (at anthesis). A sample of seed of plant variety 5210 has been deposited under NCIMB Accession No. 43656.

Plants 5211, 5212 and 5210 were also selected in 2009 (but in a different filed location), 5211 was characterized by double flower of cream light-green with a green center color (at anthesis), 5212 was characterized by double flower of cream with a light green center color (at anthesis), and 5213 was characterized by double flower in light green color (at anthesis). Plant 5453 was selected in 2009, 5209 was characterized by double flower of light yellow-green color (at anthesis).

A description of the morphological characteristics of *Gypsophila* plants selected for having green petals are presented in Table 1. As shown in Table 1, column 1 shows the number assigned to each hybrid, column 2 shows the flower size (S—small, M—medium, L—large), column 3 shows the type of flower (S-M—semi double, D—double, D-M—double multi flower), and columns 4-6 shows the description of flower color (RHS 2007) through development stages.

TABLE 1

| Hybrid Number | Flower Size (S, M, L) | Flowe Type (Double, Semi-Double) | Flower Color-development Stage 1 (RHS) | Flower Color-development Stage 2 (RHS) | Flower Color-development Stage 3 (RHS) |
|---|---|---|---|---|---|
| 5209 | M-L | D | yellow green group 154-D | outermost petals: white group 155-b and inside petals: yellow green group-154-D | white group 155-b |
| 5210 | L | D | outermost petals: yellow-green group 150-C and inside petals: yellow green group 145-A | yellow-green group 150-c | outermost petals: white group 155-d and inside petals: yellow-green group 150-B |
| 5211 | M | D | yellow-green group 145-B | outermost petals: white group 155-b and inside petals: yellow-green group 145-B | outermost petals: white group 155-b and inside petals: yellow-green group 150-B |
| 5212 | L | D | yellow-green group 145-c | outermost petals: yellow-green group 145-c and inside petals: yellow-green group 147-A | outermost petals: white group 155-d and inside petals: yellow-green group 145-c |
| 5213 | M | D | outermost petals: yellow green group-145-D and inside petals: yellow green group 146A | outermost petals: yellow green group-145-D and inside petals: yellow green group 146A | outermost petals: white group 155-b and inside petals: yellow green group 145-D |
| 5453 | M | S-M | yellow green group 149-b | yellow green group 149-d | white group 155-a |
| Million Stars | S | D | white group - 155-D | .white group - 155-D | white group - 155-D |

Example 2

Pigment Analysis in *Gypsophila* Plants

Flowers from a number of *Gypsophila* plants generated according to the present teachings were subjected to pigment analysis.

Plant Material

Flowers for isoprenoid extraction were taken from flowering plant in August 2013, those plants were planted in open filed on March 2013. The plants were grown as follow: planting density was 6 plants/m2 bed, the plants were pinched 4 weeks after planting and sprayed with 400 ppm of gibberellic acid 6 weeks after planting.

Isoprenoids Extraction and Analysis

Isoprenoids extraction was performed as previously described by Fraser et al. (2000) and by Bino et al., (2005), with small modifications: Frozen *Gypsophila* flowers powder (0.1 g) was extracted with 0.5 ml methanol containing 0.1% butylated hydroxytoluene (BHT). The samples were shaken for 5 min, then 0.5 ml of a mixture Tris-HCl buffer pH 7.5 (50 mM) was added (containing 1 M NaCl) and samples were shaken for 10 min. Cold chloroform 0.4 ml+0.1% BHT was added followed by shaking for 10 min. The samples were centrifuged for 15 min (4500 rpm). The chloroform phase was collected, when the aqueous phase of samples was re-extracted with 0.2 ml of cold chloroform mixture, then the chloroform fractions were combined and dried under N2 stream. The dry residue was re-suspended in 0.1 ml of ethyl acetate, vortexed, filtered through a 0.45 µm 4 mm PTFE membrane filter and taken for analysis. Extracts were kept at 4° C. and shielded from strong light during the entire preparation. HPLC system consisted from the Waters 2690 separation module (Waters Chromatography, Milford, Mass., USA), the Waters 2996 Photo Diode Array Detector and Waters 470 scanning fluorescence detector YMC-Pack reverse-phase C30 column (250×4.6 mm; 5 µm), coupled to a 4×3 mm C18 guard (Phenomenex) and maintained at 30° C. was used for the compounds separation. The mobile phase composition, the gradient and the flow rate was as described by Fraser et al. (2000). The UV spectra were monitored from 200 nm until 750 nm, the fluorescence detector was set for excitation at 296 nm and emission at 340 nm. Data were collected and analyzed, using the Waters Millennium32 software. Absorbance spectra and retention times of eluting peaks were compared with those of commercially available isoprenoid standards: α-tocopherol (Aldrich), Beta-Carotene (Sigma), lutein (Fluka). Zeaxanthin, violaxanthin, anthrexanthin (Apin). Peak areas of the compounds were determined at the wavelength providing maximum absorbance.

The concentrations of the compounds were calculated based on standard curves using 3 know concentrations of a commercially available standard (α-tocopherol (Aldrich), Beta-Carotene (Sigma), lutein (Fluka). Zeaxanthin, violaxanthin (Apin) (see results table).

Results

The results of isoprenoid analysis are presented in Tables 2 below and summarized in FIG. 1. Pleats of flower at different developmental stages: 1—closed flower bud, 2—flower before anthesis, 3—flower at anthesis, were collected, extracted and analyzed using HPLC. Green *Gypsophila* varieties show increase in the levels of chlorophylls, carotenoids and a-tocopherol at different developmental stages of flower compare to white flowering *Gypsophila*.

Analyses of isoprenoids content in petals of two *Gypsophila* varieties with green flower color (5210 and 5212), by contrast with the commercially known white flowering *Gypsophila* cv. Million Stars (M.S), reveled similarities in development patterns of pigments and carotenoids accumulation peaking at closed flower buds (Table 2, FIG. 1).

Beta-Carotene, chlorophyll A and chlorophyll B were identified as the major pigments in the petal of *Gypsophila* varieties tested. Pigment analysis showed that the concentration ratios of Beta-Carotene in varieties 5210 and 5212 were 4.1 and 2.9 (accordingly) higher at anthesis (stage 3), 3.5 and 3.8 higher at flower before anthesis (stage 2), 3.2 and 2.6 higher at closed flower bud (stage 1) compare to M.S, respectively. Ratios of chlorophyll-A in varieties 5210 and 5212 were 4.2 and 3 times higher at anthesis (stage 3), 3.3 and 3.5 times higher at flower before anthesis (stage 2), 3.1 and 2.5 times higher at closed flower bud (stage 1) compare to M.S, respectively. Ratios of chlorophyll B in varieties 5210 and 5212 were 5.3 and 3.9 higher at anthesis (stage 3), 3.7 and 4.2 higher at flower before anthesis (stage 2), 3.4 and 2.9 higher at closed flower bud (stage 1) compare to M.S, respectively. The carotenoids identified in *Gypsophila* petals were the lutein, b-Carotene, violexanthin, and zeaxanthin. The major pigments were Beta-Carotene and chlorophyll A, which comprised about 39-45% and 22-28% respectively, of the total pigments content in the petals of the varieties tested. The pigments chlorophyll B, alpha-tocopherol and Lutein comprised about 9-14%, 9-27% and 1-2% respectively, of the total pigments content in the petals of the varieties tested. In *Gypsophila* M.S alpha-tocopherol was identified as the third pigment, comprising 16-27% of the total pigment content, while in the green varieties 5210 and 5212 it was identified as the fourth pigment (chlorophyll B was the third) comprising 9-14% of the total pigment content. Minor amounts of violexanthin and zeaxanthin were also identified.

Ratios of alpha-tocopherol in varieties 5210 and 5212 were 1.4 and 1.3 times higher at anthesis (stage 3), 1.5 and 2 times higher at flower before anthesis (stage 2), 1.7 and 1.6 times higher at closed flower bud (stage 1) compare to M.S, respectively.

Ratios of lutein in varieties 5210 and 5212 were 7 and 4.2 times higher at anthesis (stage 3) 5.2 and 4.9 times higher at flower before anthesis (stage 2), 4 and 3 times higher at closed flower bud (stage 1) compare to M.S, respectively.

Ratios of violexanthin in varieties 5210 and 5212 were 49.1 and 19.4 times higher at anthesis (stage 3), 16.3 and 8 times higher at flower before anthesis (stage 2), 4.6 and 1.8 times higher at closed flower bud (stage 1) compare to M.S, respectively.

Ratios of zeaxanthin in varieties 5210 and 5212 were 45.3 and 29.4 times higher at anthesis (stage 3)), 113.3 and 124.7 times higher at flower before anthesis (stage 2), 11.1 and 13 times higher at closed flower bud (stage 1) compare to M.S, respectively.

TABLE 2

| Smple Name | b-caroten | chlorophyll a | chlorophyll b | a-tocopherol | Lutein | Violexanthin | Zeaxanthin |
|---|---|---|---|---|---|---|---|
| 5210-1 | 445.81 | 282.28 | 133.60 | 93.41 | 19.51 | 9.60 | 5.84 |
| 5210-2 | 390.56 | 240.81 | 118.34 | 87.42 | 17.41 | 9.16 | 4.95 |
| 5210-3 | 361.40 | 217.15 | 107.84 | 85.41 | 16.11 | 8.99 | 3.90 |

TABLE 2-continued

| Smple Name | b-caroten | chlorophyll a | chlorophyll b | a-tocopherol | Lutein | Violexanthin | Zeaxanthin |
|---|---|---|---|---|---|---|---|
| 5212-1 | 363.11 | 224.27 | 115.41 | 89.47 | 14.44 | 3.81 | 6.82 |
| 5212-2 | 421.51 | 252.80 | 134.27 | 116.41 | 16.31 | 4.51 | 5.45 |
| 5212-3 | 260.07 | 155.25 | 80.30 | 84.23 | 9.75 | 3.56 | 2.53 |
| MS-1 | 140.93 | 90.26 | 39.65 | 55.32 | 4.86 | 2.09 | 0.53 |
| MS-2 | 110.48 | 72.01 | 31.81 | 59.18 | 3.35 | 0.56 | 0.04 |
| MS-3 | 88.48 | 51.75 | 20.33 | 62.48 | 2.32 | 0.18 | 0.09 |

In conclusion, all *Gypsophila paniculata* or any *Gypsophila* hybrid in the market has white or light pink mono color petals. The present invention provides the development of the first *Gypsophila* varieties with unique coloration, including for example, green, cream, and yellow/green/orange and/or multi-color petals.

From these introductions and using breeding methodology, the inventor can introduce new colors and or multi-colors by crossing these *Gypsophila* plants with pink varieties.

What is claimed is:

1. A *Gypsophila paniculata* plant comprising a flower having an altered phenotype, said flower having said altered phenotype comprises:
   (a) an elevated amount of Beta-Carotene; and
   (b) an elevated amount of chlorophyll A, an elevated amount of chlorophyll B, or both, wherein:
      (i) said elevated amount of Beta-Carotene is at least 2 times the concentration of beta-Carotene compared to the concentration of Beta-Carotene in *Gypsophila* cv. Million Stars (M.S) flower;
      (ii) said elevated amount of chlorophyll A, said elevated amount of chlorophyll B, or both are elevated compared to chlorophyll A amount, chlorophyll B amount, or both in said *Gypsophila* cv. Million Stars (M.S) flower,
   said flower having an altered phenotype and said *Gypsophila* cv. Million Stars (M.S) flower are at the same developmental stage.

2. The plant of claim 1, wherein said *Gypsophila* flower is at anthesis or is at the closed bud phase.

3. The plant of claim 1, wherein said at least twice is at least four times.

4. The plant of claim 1, wherein said elevated amount of chlorophyll A is at least twice the concentration of chlorophyll A compared to the concentration of chlorophyll A in said *Gypsophila* cv. Million Stars (M.S) flower, said elevated amount of chlorophyll B is at least twice the concentration of chlorophyll B compared to the concentration of chlorophyll B in said *Gypsophila* cv. Million Stars (M.S) flower, or both.

5. The plant of claim 1, wherein said flower having an altered phenotype comprises: from 0.5 to 4% Lutein of the total pigments, carotenoids or both content in a petal, from 30 to 50% Beta-Carotene of the total pigments, carotenoids or both content in a petal, from 8 to 30% alpha-Tocopherol of the total pigments and/or carotenoids content in a petal, or any combination thereof.

6. The plant of claim 1, wherein at least 15% of a petal's surface area of said flower having an altered phenotype is green, yellow, orange or any combination thereof.

7. The plant of claim 1, wherein at least 10% of a petal's surface area of said flower having an altered phenotype is white, yellow, or both.

* * * * *